US009198711B2

(12) United States Patent
Joseph

(10) Patent No.: US 9,198,711 B2
(45) Date of Patent: Dec. 1, 2015

(54) ELECTROSURGICAL SYSTEM FOR COMMUNICATING INFORMATION EMBEDDED IN AN AUDIO TONE

(75) Inventor: Daniel A. Joseph, Golden, CO (US)

(73) Assignee: Covidien LP, Mansfield, MA (US)

( * ) Notice: Subject to any disclaimer, the term of this patent is extended or adjusted under 35 U.S.C. 154(b) by 924 days.

(21) Appl. No.: 13/427,111

(22) Filed: Mar. 22, 2012

(65) Prior Publication Data
US 2013/0253501 A1    Sep. 26, 2013

(51) Int. Cl.
*A61B 18/00* (2006.01)
*A61B 18/12* (2006.01)
*A61B 18/14* (2006.01)

(52) U.S. Cl.
CPC ......... *A61B 18/1206* (2013.01); *A61B 18/1445* (2013.01); *A61B 2018/0063* (2013.01); *A61B 2018/00577* (2013.01); *A61B 2018/00589* (2013.01); *A61B 2018/00601* (2013.01); *A61B 2018/1455* (2013.01)

(58) Field of Classification Search
USPC .................................................. 704/270, 275
See application file for complete search history.

(56) References Cited

U.S. PATENT DOCUMENTS

| | | | |
|---|---|---|---|
| 5,311,581 A | 5/1994 | Merriam et al. | |
| 5,729,596 A | 3/1998 | Reeder et al. | |
| 5,774,529 A | 6/1998 | Johannsen et al. | |
| 5,987,105 A | 11/1999 | Jenkins et al. | |
| 5,997,170 A | 12/1999 | Brodbeck | |
| 6,147,601 A | 11/2000 | Sandelman et al. | |
| 6,160,477 A | 12/2000 | Sandelman et al. | |
| 6,211,782 B1 | 4/2001 | Sandelman et al. | |
| 6,327,365 B1 | 12/2001 | Kiger, II | |
| 6,697,466 B2 | 2/2004 | Howard et al. | |
| 7,240,010 B2 | 7/2007 | Papadimitriou et al. | |
| 7,245,708 B2 | 7/2007 | Forrest et al. | |
| 7,280,643 B2 | 10/2007 | Howard et al. | |
| 7,403,871 B2 | 7/2008 | Papadimitriou et al. | |
| D574,323 S | 8/2008 | Waaler | |

(Continued)

FOREIGN PATENT DOCUMENTS

| | | |
|---|---|---|
| DE | 179607 | 3/1905 |
| DE | 1099658 | 2/1961 |

(Continued)

OTHER PUBLICATIONS

U.S. Appl. No. 10/406,690, filed Apr. 3, 2003, Robert J. Behnke, II.

(Continued)

*Primary Examiner* — Abul Azad

(57) ABSTRACT

An electrosurgical system is provided. The electrosurgical system includes an electrosurgical generator including a computer having one or more microprocessors in operable communication with memory for storing information pertaining to the electrosurgical generator. An audio output module is in operable communication with the computer and configured to generate an audio output having the information pertaining to the electrosurgical generator embedded therein. A speaker is in operable communication with the audio output module for outputting the audio output. A recording device is configured to record the audio output. An audio collector is configured to receive the audio output from the recording device and decipher the embedded audio so that the information pertaining to the electrosurgical generator may be utilized for future use.

15 Claims, 2 Drawing Sheets

(56) References Cited

U.S. PATENT DOCUMENTS

| | | | |
|---|---|---|---|
| 7,587,178 B2 | 9/2009 | Marquardt | |
| 7,845,537 B2* | 12/2010 | Shelton et al. | 227/180.1 |
| 8,050,874 B2 | 11/2011 | Papadimitriou et al. | |
| 8,086,425 B2 | 12/2011 | Papadimitriou et al. | |
| 8,204,189 B2 | 6/2012 | Rhodes et al. | |
| 2008/0004616 A1* | 1/2008 | Patrick | 606/38 |
| 2010/0193569 A1* | 8/2010 | Yates et al. | 227/176.1 |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4206433 | 9/1993 |
| DE | 4339049 | 5/1995 |
| DE | 19506363 | 8/1996 |
| DE | 19717411 | 11/1998 |
| DE | 19848540 | 5/2000 |
| DE | 10 2008058737 | 4/2010 |
| EP | 246350 | 11/1987 |
| EP | 267403 | 5/1988 |
| EP | 296777 | 12/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 882955 | 12/1998 |
| EP | 1051948 | 11/2000 |
| EP | 1366724 | 1/2006 |
| EP | 880220 | 6/2006 |
| EP | 1776929 | 4/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| JP | 63 005876 | 1/1988 |
| JP | 2002-065690 | 3/2002 |
| SU | 166452 | 1/1965 |
| SU | 727201 | 4/1980 |
| WO | WO02/11634 | 2/2002 |
| WO | WO02/45589 | 6/2002 |
| WO | WO03/090635 | 11/2003 |
| WO | WO2006/050888 | 5/2006 |
| WO | WO2008/053532 | 5/2008 |

OTHER PUBLICATIONS

U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 13/048,639, filed Mar. 15, 2011, James S. Cunningham.
U.S. Appl. No. 13/049,459, filed Mar. 16, 2011, James H. Orszulak.
U.S. Appl. No. 13/050,770, filed Mar. 17, 2011, Robert B. Smith.
U.S Appl. No. 13/085,258, filed Apr. 12, 2011, Ronald J. Podhajsky.
U.S Appl. No. 13/085,278, filed Apr. 12, 2011, James A. Gilbert.
U.S Appl. No. 13/118,973, filed May 31, 2011, James H. Orszulak.
U.S Appl. No. 13/186,092, filed Jul. 19, 2011, George J. Collins.
U.S Appl. No. 13/186,107, filed Jul. 19, 2011, George J. Collins.
U.S Appl. No. 13/186,121, filed Jul. 19, 2011, George J. Collins.
U.S Appl. No. 13/195,607, filed Aug. 1, 2011, James H. Orszulak.
U.S Appl. No. 13/221,424, filed Aug. 30, 2011, James E. Krapohl.
U.S. Appl. No. 13/228,996, filed Sep. 9, 2011, Robert B. Smith.
U.S Appl. No. 13/236,997, filed Sep. 20, 2011, Robert J. Behnke, II.
U.S Appl. No. 13/237,068, filed Sep. 20, 2011, Robert J. Behnke, II.
U.S Appl. No. 13/237,187, filed Sep. 20, 2011, Robert J. Behnke, II.
U.S Appl. No. 13/237,342, filed Sep. 20, 2011, Robert J. Behnke, II.
U.S. Appl. No. 13/237,488, filed Sep. 20, 2011, Robert J. Behnke, II.
U.S. Appl. No. 13/247,043, filed Sep. 28, 2011, Donald W. Heckel.
U.S. Appl. No. 13/358,129, filed Jan. 25, 2012, Joseph D. Brannan.
U.S. Appl. No. 13/360,140, filed Jan. 27, 2012, James E. Krapohl.
U.S. Appl. No. 13/426,204, filed Mar. 21, 2012, Robert B. Smith.
U.S. Appl. No. 13/427,111, filed Mar. 22, 2012, Daniel A. Joseph.
U.S. Appl. No. 13/442,460, filed Apr. 9, 2012, James E. Krapohl.
U.S. Appl. No. 13/446,096, filed Apr. 13, 2012, James H. Orszulak.
U.S. Appl. No. 13/469,960, filed May 11, 2012, Robert J. Behnke, II.
U.S. Appl. No. 13/483,815, filed May 30, 2012, Jeffrey R. Unger.
U.S. Appl. No. 13/485,083, filed May 31, 2012, Robert J. Behnke, II.
U.S. Appl. No. 13/526,205, filed Jun. 18, 2012, Jeffrey L. Jensen.
U.S. Appl. No. 13/540,347, filed Jul. 2, 2012, Ronald J. Podhajsky.
U.S. Appl. No. 13/593,550, filed Aug. 24, 2012, Ronald J. Podhajsky.
U.S. Appl. No. 13/584,192, filed Aug. 13, 2012, Joseph D. Brannan.
U.S. Appl. No. 13/587,400, filed Aug. 16, 2012, James H. Orszulak.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.

(56) References Cited

OTHER PUBLICATIONS

Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.
Zlatanovic M., "Sensors in Diffusion Plasma Processing" Microelectronics 1995; Proceedings 1995; $20^{th}$ International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . " Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001494.9 dated Aug. 25, 2010.
International Search Report EP 07001494.9 extended dated Mar. 7, 2011.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.
International Search Report EP09004250.8 dated Aug. 2, 2010.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP09763515.5 dated Nov. 29, 2011.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report EP10164740.2 dated Aug. 3, 2010.
International Search Report EP10171787.4 dated Nov. 18, 2010.
International Search Report EP10172636.2 dated Dec. 6, 2010.
International Search Report EP10174476.1 dated Nov. 12, 2010.
International Search Report EP10178287.8 dated Dec. 14, 2010.
International Search Report EP10179305.7 dated Aug. 23, 2011.
International Search Report EP10179321.4 dated Mar. 18, 2011.
International Search Report EP10179353.7 dated Dec. 21, 2010.
International Search Report EP10179363.6 dated Jan. 12, 2011.
International Search Report EP10180004.3 dated Jan. 5, 2011.
International Search Report EP10180964.8 dated Dec. 22, 2010.
International Search Report EP10180965.5 dated Jan. 26, 2011.
International Search Report EP10181018.2 dated Jan. 26, 2011.
International Search Report EP10181060.4 dated Jan. 26, 2011.
International Search Report EP10182003.3 dated Dec. 28, 2010.
International Search Report EP10182005.8 dated Jan. 5, 2011.
International Search Report EP10188190.2 dated Nov. 22, 2010.
International Search Report EP10191319.2 dated Feb. 22, 2011.
International Search Report EP10195393.3 dated Apr. 11, 2011.
International Search Report EP11006233.8 dated Feb. 2, 2012.
International Search Report EP11155959.7 dated Jun. 30, 2011.
International Search Report EP11155960.5 dated Jun. 10, 2011.
International Search Report EP11168660 dated Sep. 28, 2011.
International Search Report EP11170959.8 dated Dec. 9, 2011.
International Search Report EP11173562.7 dated Nov. 24, 2011.
International Search Report EP11182150.0 dated Nov. 17, 2011.
International Search Report EP11188798.0 dated Dec. 27, 2011.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/USO4/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.

\* cited by examiner

ELECTROSURGICAL SYSTEM FOR COMMUNICATING INFORMATION EMBEDDED IN AN AUDIO TONE

BACKGROUND

1. Technical Field

The present disclosure relates to electrosurgical system. More particularly, the present disclosure relates to an electrosurgical system including an electrosurgical generator configured to communicate information embedded in an audible tone generated by the electrosurgical generator.

2. Description of Related Art

Electrosurgical systems that are configured to electrosurgically treat tissue are well known in the art. Electrosurgical systems, typically, include an electrosurgical generator that is configured to couple and provide electrosurgical energy, e.g., RF and/or microwave energy, to one or more suitable types of electrosurgical instruments, e.g., electrosurgical forceps.

For example, and in one particular instance, the electrosurgical generator and corresponding electrosurgical instrument may be configured to seal tissue. In this instance, the electrosurgical generators may be configured to provide electrosurgical energy to the electrosurgical instrument for specified time period and intensity level, commonly referred to as a "duty cycle." The electrosurgical generators may be configured to provide an audible indication to an end user, e.g., a surgeon. For example, and in certain instances, the electrosurgical generators may be configured to provide an audible tone that represents the beginning of a duty cycle and an audible tone that represents an end of the duty cycle.

SUMMARY

While the aforementioned electrosurgical systems provide an effective method in electrosurgically treating tissue, it may prove advantageous to provide an electrosurgical generator that is configured to embed information pertaining to the electrosurgical generator, electrosurgical instrument coupled thereto and/or an electrosurgical procedure in an audible tone generated by the electrosurgical generator.

Aspects of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

An aspect of the present disclosure provides an electrosurgical system configured for use in performing an electrosurgical procedure. The electrosurgical system includes an electrosurgical generator including a computer having one or more microprocessors in operable communication with memory for storing information pertaining to the electrosurgical generator. An audio output module is in operable communication with the computer and configured to generate an audio output having the information pertaining to the electrosurgical generator embedded therein. The embedded information may be encrypted. A speaker is in operable communication with the audio output module for outputting the audio output. An audio collector is configured to receive the audio output from the speaker and decipher the embedded audio so that the information pertaining to the electrosurgical generator may be utilized for future use.

The audio collector may be components of the electrosurgical generator. In this particular instance, the deciphered information may be stored in memory of the electrosurgical generator.

The audio collector may include a computer system including a processor, memory, one or more storage devices, one or more input modules, one or more output modules and one or more communication ports configured to couple to the recording device.

The audio collector may be a component of a video recording system configured to video-tape the electrosurgical procedure.

The information pertaining to the electrosurgical generator may include, but is not limited to date and time of an electrosurgical procedure, activation time of one of the electrosurgical generator and the electrosurgical instrument, type of electrosurgical instrument connected to the electrosurgical generator, electrosurgical generator serial number, amount of electrosurgical energy delivered to electrosurgical instrument, amount of electrosurgical energy delivered to tissue, and whether the electrosurgical generator was shut off manually via a shut off button on the electrosurgical generator or automatically as a result of an end of a duty cycle.

Another aspect of the present disclosure provides an electrosurgical generator configured to provide electrosurgical energy to an electrosurgical instrument. The electrosurgical instrument includes a computer having one or more microprocessors that are in operable communication with memory for storing information pertaining to either the electrosurgical generator or the electrosurgical instrument. An audio output module is configured to generate an audio output having the information pertaining to one of the electrosurgical generator and the electrosurgical instrument embedded therein. The embedded information may be encrypted. One or more speakers are in operable communication with the audio output module for outputting the audio output received from the audio output module.

In certain instances, the electrosurgical generator is in operable communication with an audio collector configured to record the audio output from the speaker(s) and decipher the embedded audio so that the information pertaining to the electrosurgical generator and the electrosurgical instrument may be utilized for future use.

In certain stances, the audio collector may be a component of a video recording system configured to video-tape the electrosurgical procedure. In other instances, the information pertaining to the electrosurgical generator may include, but is not limited to date and time of an electrosurgical procedure, activation time of one of the electrosurgical generator and the electrosurgical instrument, type of electrosurgical instrument connected to the electrosurgical generator, electrosurgical generator serial number, amount of electrosurgical energy delivered to electrosurgical instrument, amount of electrosurgical energy delivered to tissue, and whether the electrosurgical generator was shut off manually via a shut off button on the electrosurgical generator or automatically as a result of an end of a duty cycle.

Another aspect of the present disclosure provides a method of transferring information pertaining to an electrosurgical generator and an electrosurgical instrument. An audio output is generated and embedded with information pertaining to the electrosurgical generator and electrosurgical instrument. The audio output is transmitted from the electrosurgical generator. The audio output is recorded and, subsequently deciphered.

An audio output module may be provided to generate and, subsequently, embed the audio output with the information pertaining to one of the electrosurgical generator and the electrosurgical instrument. A speaker may be provided to transmit the audio output. An audio collector is provided to record and decipher the embedded audio so that the information pertaining to the electrosurgical generator may be utilized for future use. The audio collector may be a component of a video recording system configured to video-tape the electrosurgical procedure.

The method may include encrypting the embedded information prior to transmitting the audio output. The information pertaining to the electrosurgical generator may include, but is not limited to date and time of an electrosurgical procedure, activation time of one of the electrosurgical generator and the electrosurgical instrument, type of electrosurgical instrument connected to the electrosurgical generator, electrosurgical generator serial number, amount of electrosurgical energy delivered to electrosurgical instrument, amount of electrosurgical energy delivered to tissue, and whether the electrosurgical generator was shut off manually via a shut off button on the electrosurgical generator or automatically as a result of an end of a duty cycle.

The method may also include regenerating the deciphered information into one of an audible and visual perceivable medium.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
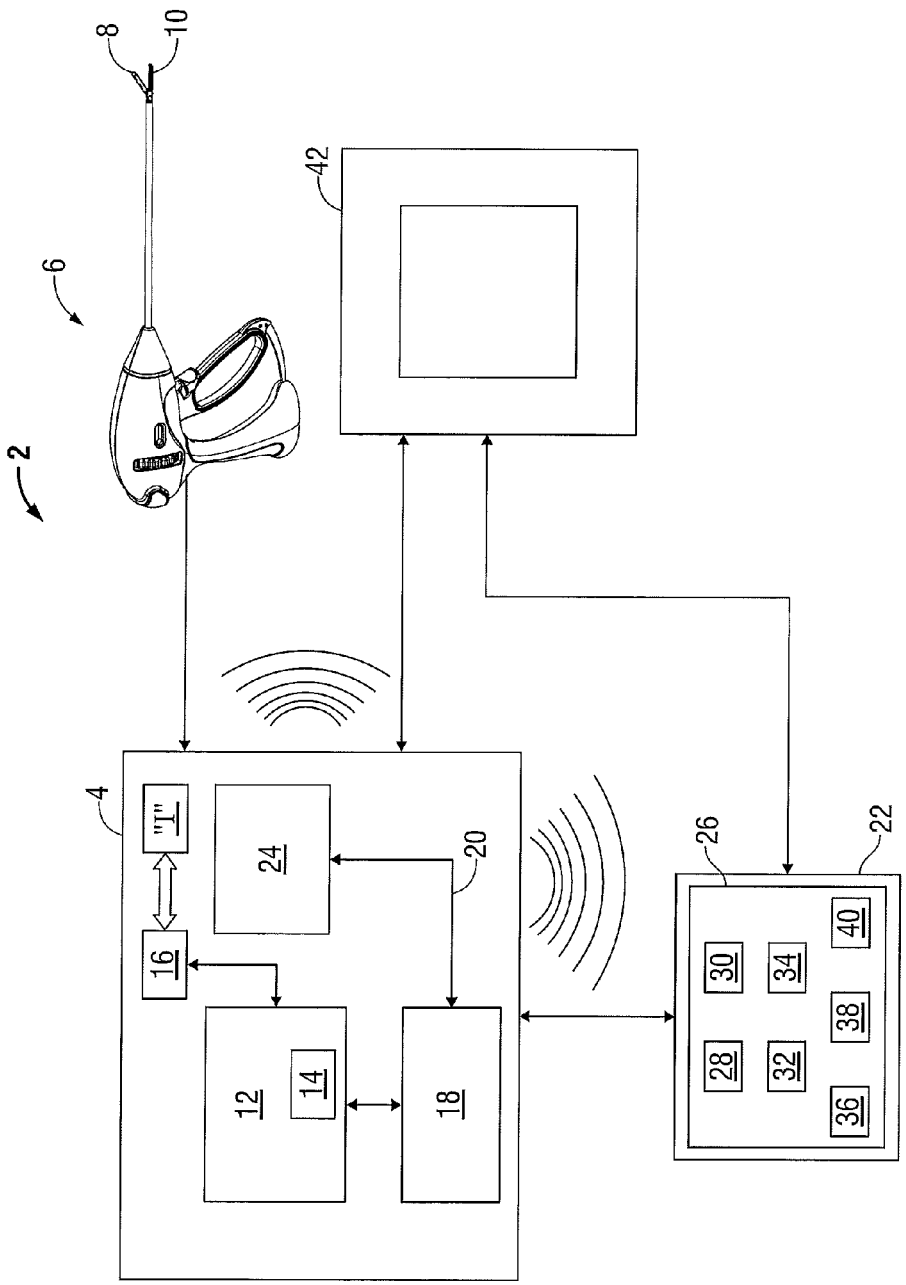
FIG. 1 is a block diagram of an electrosurgical system configured for use with an electrosurgical instrument according to an embodiment of the present disclosure.

Turning now to FIG. 1, an electrosurgical system 2 is illustrated including an electrosurgical generator 4 and an electrosurgical device (e.g., an electrosurgical forceps, electrosurgical stapler, etc.) configured to electrosurgically treat tissue. For the purposes herein, it is assumed that the electrosurgical device is a bipolar endoscopic electrosurgical forceps 6.

Continuing with reference to FIG. 1, electrosurgical generator 4 includes electronic circuitry that generates radio frequency power for various electrosurgical procedures (e.g., sealing, cutting, coagulating, or ablating tissue). The electrosurgical generator 4 may be configured to function in either monopolar or bipolar modes of operation. A plurality of outputs (not explicitly shown) may be configured for interfacing with the forceps 6 and/or other various electrosurgical instruments and or devices, e.g., a return pad, etc.

In accordance with the instant disclosure, and depending on the specific type of electrosurgical procedures that the electrosurgical generator 4 is set to provide electrosurgical energy for, the electrosurgical generator 4 utilizes one or more duty cycles to effect tissue. For example, and in one particular embodiment, a duty cycle may include applying electrosurgical energy to tissue grasped between jaw members 8, 10 of the forceps 6 for a predetermined amount of time to seal tissue. At the end of the duty cycle, the sealed tissue may be severed by either a cutting electrode or knife.

In accordance with the present disclosure, the electrosurgical generator 4 provides an audible tone (of suitable frequency) to indicate to a user when to begin applying electrosurgical energy to tissue and when to stop applying electrosurgical energy to tissue such that an effective tissue seal may be achieved. In embodiments, the audio tone may be perceivable to a user. Alternately, the electrosurgical generator 4 may be configured to provide an audible tone that is not perceivable to a user, e.g., an audible tone in an ultrasonic frequency range. In either instance, the electrosurgical generator 4 is configured to embed the audible tone with information that is pertinent to the electrosurgical generator 4, the forceps 6 and/or an electrosurgical procedure.

Electrosurgical generator 4 includes a computer 12 having one or more microprocessors 14 in operable communication with memory 16 (in embodiments, electrosurgical generator 4 may include flash memory 16) for storing information "I" pertaining to the electrosurgical generator 4 (FIG. 1). The information "I" pertaining to the electrosurgical generator 4 may include, but is not limited to date and time of an electrosurgical procedure, activation time of the electrosurgical generator 4 and/or the forceps 6, type of electrosurgical instrument that is connected to the electrosurgical generator 4, serial number of the electrosurgical generator 4, amount of electrosurgical energy delivered to the forceps 6, amount of electrosurgical energy delivered to tissue, and whether the electrosurgical generator 4 was shut off manually via a shut off button on the electrosurgical generator 4 or automatically as a result of an end of a duty cycle. Those skilled in the art will appreciate the various types of processors and memory that can be used for storing information "I." For example, an embodiment of electrosurgical generator 4 may include a single-board computer 12 that includes the processor 14 and memory 16. Such single-board computers are commercially available. Alternatively, the electrosurgical generator 4 may include a microcontroller that functions as the processor 14.

In embodiments, electrosurgical generator 4 may include inputs (not shown) that allow a user to enter user input to the electrosurgical generator 4. The inputs may, for example, be a set of buttons, switches, sensors, etc. Those skilled in the art will appreciate the various kinds of inputs that can be used for a user to enter user input. Through the inputs the user may include specific information to be embedded on the audible tone that is generated by the electrosurgical generator 4.

An audio output module 18 is in operable communication with the computer 12 and is configured to generate an audio output 20 that has information "I" embedded therein (FIG. 1). In certain embodiments, the audio output 20 is perceivable to a user, recorded, and decoded by an audio collector 22, described in greater detail below. In operation, audio output module 18 compiles relevant information stored in memory 16 that is to be embedded with the audio output 20. That is, audio output module 18 translates the information "I" stored in memory 16 into a suitable audio output format such that the information "I" may be embedded with the audio output 20. Once the information "I" has been embedded with the audio output 20 it is output through a speaker 24 (FIG. 1). In certain embodiments, the embedded audio output 20 may be encrypted to protect the embedded audio output 20 during transfer thereof.

Speaker 24 with supporting speaker components, e.g., a driving circuit (not explicitly shown) is in operable communication with the audio output module 18 for outputting the embedded audio output 20 (FIG. 1). Speaker components may include one or more sound cards with a speaker jack to which a speaker 24 may be attached. Further, the speaker 24 and speaker components may be embodied in an integrated circuit capable of producing sound. Those skilled in the art will appreciate the commercially available speakers and sound components that may be utilized with the electrosurgical generator 4 to produce sound.

Continuing with reference to FIG. 1, audio collector 22 may use a computer 26 to recognize the tones, the tone sequences, the tone frequencies, etc., and to receive and decode the embedded audio output 20 output by the speaker 24. For example, and as illustrated in FIG. 1, the audio collector 22 may include computer 26 that is configured to listen for the embedded audio output 20 generated by the electrosurgical generator 4 and also configured to decode the embedded audio output 20. The decoded information is placed in memory 30 for future use thereof. Typical components of a computer 26 may include a processor 28, memory 30, a storage device 32, input devices 34 and output devices 36. In certain embodiments, one or more communication ports 38 may also be included in the audio controller 22 and/or computer 26. It will be appreciated by those skilled in the art that many more components may be included in the audio collector 22 and/or computer 20. For example, various output devices may include without limitation a monitor, speakers, a printer, etc.

Audio controller 22 includes a microphone 40 (FIG. 1) including supporting components associated therewith. Microphone 40 is used to detect the embedded audio output 20 and includes audio processing software (not shown) that used to decipher the embedded audio output 20 transmitted from the speaker 24 of the electrosurgical generator 4. Microphone 40 (and supporting components associated therewith) may be configured to communicate with one or more components of the computer 26 of the audio controller 22. To provide the embedded audio output 20 to the audio collector 22, the user may simply place the audio collector 22 in a vicinity of speaker 24 of the electrosurgical generator 4.

In certain instances, the audio controller 22 may configured to function as part of an optional video-recording system 42. Other than including the previously described capabilities of the audio controller 22, video-recording system 42 functions similar to conventional video-recording systems.

Figure 2:
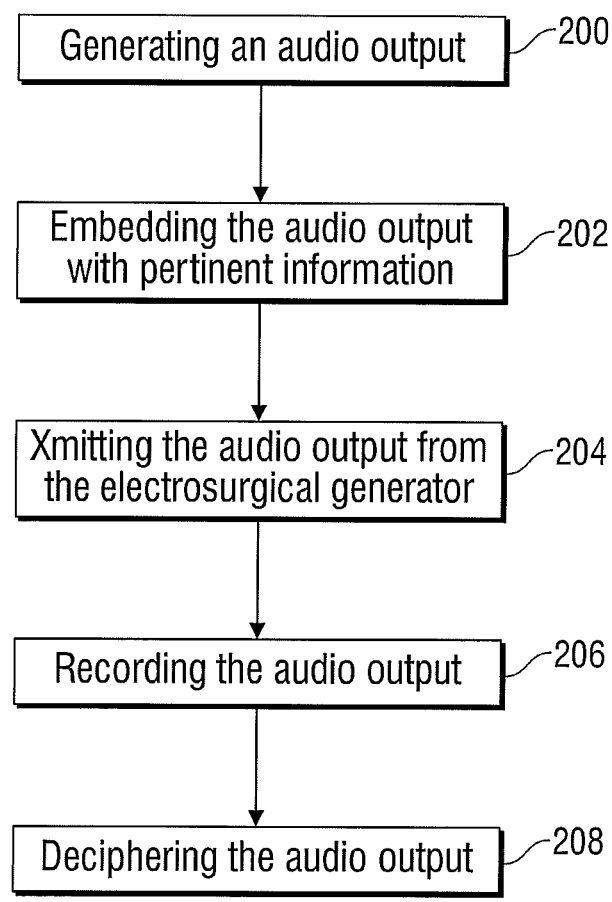
FIG. 2 is a flowchart of a method for transferring information pertaining to an electrosurgical generator and an electrosurgical instrument configured for use with the electrosurgical system depicted in FIG. 1.

Operation of electrosurgical system 2 is described in terms of a method for transferring information pertaining to an electrosurgical generator 4 and an electrosurgical instrument 6. Audio output module 18 is utilized to generate an audio output, see FIG. 2 at step 200. The audio output is embedded with information pertaining to the electrosurgical generator 4 and electrosurgical instrument 6, see FIG. 2 at step 202. The embedded audio output 20 is communicated to the speaker 24 that transmits the embedded audio output 20, see FIG. 2 at step 204.

The microphone 40 of the audio controller detects the embedded audio output 20. The audio controller 22 records the embedded audio output tone, deciphers the embedded audio output 20 and, subsequently, stores the deciphered information into memory 30 see FIG. 2 at steps 206 and 208. Thereafter, the deciphered information "I" may be retrieved from memory 30 for future use thereof. For example, the deciphered information may be regenerated into either an audible and/or visual perceivable medium, e.g., monitor, speakers, a printer, etc.

From the foregoing and with reference to the various figure drawings, those skilled in the art will appreciate that certain modifications can also be made to the present disclosure without departing from the scope of the same. For example, and as noted above, the electrosurgical system 2 may be configured to include video recording system 42. This embodiment may be particularly useful in reviewing a surgical procedure, a training environment or for troubleshooting the electrosurgical generator 4 and/or forceps 6.

For example, in use, a surgeon grasps tissue and activates the electrosurgical generator 4. The electrosurgical generator 4 emits an embedded audible tone 20, but the surgeon does not hear the end of the embedded audible tone 20 and prematurely stops the transmission of electrosurgical energy to tissue to only partially treat the tissue, e.g., an ineffective tissue seal.

Subsequently, the surgeon utilizes a knife blade (or other suitable device) to sever the "partially" treated tissue. As can be appreciated, there exists a likelihood that the severed and "partially" treated tissue may bleed or burst, which, in turn, may cause patient concern.

With the presently disclosed disclosure, the embedded audio output 20 can be reviewed to determine when the surgeon shut off the electrosurgical generator 4. That is, to determine if the surgeon prematurely ended the duty-cycle or if the electrosurgical generator 4 was not functioning properly, thereby removing the guess-work as to who or what was at fault.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical system configured for use in performing an electrosurgical procedure, comprising:
   an electrosurgical generator including:
      a computer having at least one microprocessor in operable communication with memory for storing information pertaining to the electrosurgical generator;
      an audio output module in operable communication with the computer and configured to generate an audio output having the information pertaining to the electrosurgical generator embedded therein;
      a speaker in operable communication with the audio output module for outputting the audio output; and
      an audio collector configured to receive the audio output from the speaker and decipher the embedded audio output so that the information pertaining to the electrosurgical generator may be utilized for future use.

2. An electrosurgical system according to claim 1, wherein the embedded information is encrypted.

3. An electrosurgical system according to claim 1, wherein the audio collector is a component of the electrosurgical generator and wherein the deciphered information is stored in memory of the electrosurgical generator.

4. An electrosurgical system according to claim 1, wherein the audio collector includes a computer system including a processor, memory, at least one storage device, at least one input module, at least one output module and at least one communication port configured to couple to a recording device.

5. An electro surgical system according to claim 4, wherein the audio collector is a component of a video recording system configured to video-tape the electrosurgical procedure.

6. An electrosurgical system according to claim 1, wherein the information pertaining to the electrosurgical generator is selected from the group consisting of date and time of an electrosurgical procedure, activation time of one of the electrosurgical generator and an electrosurgical instrument, type of electrosurgical instrument connected to the electrosurgical generator, electrosurgical generator serial number, amount of electrosurgical energy delivered to electrosurgical instrument, amount of electrosurgical energy delivered to tissue, and whether the electrosurgical generator was shut off manually via a shut off button on the electrosurgical generator or automatically as a result of an end of a duty cycle.

7. An electrosurgical generator configured to provide electrosurgical energy to an electrosurgical instrument, comprising:
- a computer having at least one microprocessor in operable communication with a memory for storing information pertaining to at least one of the electrosurgical generator or the electrosurgical instrument;
- an audio output module configured to generate an audio output having the information pertaining to at least one of the electrosurgical generator or the electrosurgical instrument embedded therein;
- at least one speaker in operable communication with the audio output module for outputting the audio output received from the audio output module; and
- an audio collector configured to record the audio output from the at least one speaker and decipher the embedded audio to obtain the information pertaining to at least one of the electrosurgical generator or the electrosurgical instrument.

8. An electrosurgical generator according to claim 7, wherein the embedded information is encrypted.

9. An electrosurgical generator according to claim 7, wherein the audio collector includes a computer system including a processor, a memory, at least one storage device, at least one input module, at least one output module, and at least one communication port configured to couple to a recording device.

10. An electrosurgical generator according to claim 9, wherein the audio collector is a component of a video recording system.

11. An electrosurgical generator according to claim 7, wherein the information pertaining to the electrosurgical generator and the electrosurgical instrument is selected from the group consisting of date and time of an electrosurgical procedure, activation time of one of the electrosurgical generator and the electrosurgical instrument, type of electrosurgical instrument connected to the electrosurgical generator, electrosurgical generator serial number, amount of electrosurgical energy delivered to electrosurgical instrument, amount of electrosurgical energy delivered to tissue, and whether the electrosurgical generator was shut off manually via a shut off button on the electrosurgical generator or automatically as a result of an end of a duty cycle.

12. A method for transferring information pertaining to an electrosurgical generator and an electrosurgical instrument, comprising:
- generating an audio output through an audio output module;
- embedding at the audio output module the audio output with information pertaining to at least one of the electrosurgical generator or the electrosurgical instrument;
- transmitting the audio output from the electrosurgical generator through a speaker;
- recording the audio output at an audio collector; and
- deciphering the audio output at the audio collector to obtain the information pertaining to at least one of the electrosurgical generator or the electrosurgical instrument.

13. A method according to claim 12, further including encrypting the embedded information prior to transmitting the audio output.

14. A method according to claim 12, wherein the information pertaining to the electrosurgical generator is selected from the group consisting of date and time of an electrosurgical procedure, activation time of one of the electrosurgical generator and the electrosurgical instrument, type of electrosurgical instrument connected to the electrosurgical generator, electrosurgical generator serial number, amount of electrosurgical energy delivered to electrosurgical instrument, amount of electrosurgical energy delivered to tissue, and whether the electrosurgical generator was shut off manually via a shut off button on the electrosurgical generator or automatically as a result of an end of a duty cycle.

15. A method according to claim 12, further including regenerating the deciphered information into one of an audible and visual perceivable medium.

* * * * *